United States Patent [19]
Gerlach et al.

[11] Patent Number: 4,943,988
[45] Date of Patent: Jul. 24, 1990

[54] X-RAY DIAGNOSTICS INSTALLATION HAVING AN IMAGE INTENSIFIER VIDEO CHAIN

[75] Inventors: Hans-Juergen Gerlach, Erlangen; Horst Aichinger, Fuerth, both of Fed. Rep. of Germany

[73] Assignee: Siemens Aktiengesellschaft, Berlin and Munich, Fed. Rep. of Germany

[21] Appl. No.: 426,977

[22] Filed: Oct. 26, 1989

[30] Foreign Application Priority Data

Dec. 2, 1988 [EP] European Pat. Off. ........ 88120176.8

[51] Int. Cl.$^5$ .............................................. H05G 1/44
[52] U.S. Cl. ...................................... 378/108; 378/99
[58] Field of Search ...................... 378/96, 97, 108, 99, 378/206; 358/111

[56] References Cited

U.S. PATENT DOCUMENTS

| | | | |
|---|---|---|---|
| 3,912,936 | 10/1975 | Cunninghame et al. | 378/151 |
| 4,335,307 | 6/1982 | De Vries et al. | 378/99 |
| 4,354,112 | 10/1982 | Nishio | 378/99 |
| 4,472,826 | 9/1984 | van de Ven | 378/99 |
| 4,517,594 | 5/1985 | Horbaschek | 358/111 |
| 4,809,309 | 2/1989 | Beekmans | 358/111 |

FOREIGN PATENT DOCUMENTS

| | | |
|---|---|---|
| 0038666 | 10/1981 | European Pat. Off. . |
| 0087843 | 9/1983 | European Pat. Off. . |
| 0217456 | 4/1987 | European Pat. Off. . |
| 2476949 | 8/1981 | France . |
| 58-57448 | 10/1984 | Japan . |

*Primary Examiner*—Craig E. Church
*Assistant Examiner*—John C. Freeman
*Attorney, Agent, or Firm*—Hill, Van Santen, Steadman & Simpson

[57] ABSTRACT

An x-ray diagnostics installation having an image intensifier video chain which back-projects a region of primary medical interest within an x-ray image into the overall video image is provided with fiber optics and opto-electronic transducers which are actuated by a switching bank in accordance with the desired shape and position of the region of primary interest. The transducers and switching arrangment can be removed, so that the output image from the x-ray image intensifier can be viewed at the output side of the fiber optics.

2 Claims, 4 Drawing Sheets

X-RAY DIAGNOSTICS INSTALLATION HAVING AN IMAGE INTENSIFIER VIDEO CHAIN

BACKGROUND OF THE INVENTION

1. Field of the Invention

The present invention is directed to an x-ray diagnostics installation having an image intensifier video chain, wherein a region of primary medical interest can be displayed with the overall image.

2. Description of the Prior Art

X-ray installations are known in the art wherein the output image of the x-ray image intensifier is supplied to a video camera, which then supplies the image, with appropriate processing, to a video display. It is also known to intercept the light image with fiber optics having an input end disposed between the image intensifier and the video camera. Individual opto-electric transducers are allocated to the respective light waveguides in the fiber optics system and predetermined transducers are selectively switched (i.e., caused to emit light) so as to form a signal corresponding to the average image brightness in a predetermined region of the overall image.

The detector formed by the transducers may consist of a matrix of photo-elements, with a specific geometrical arrangement of photo-elements being activateable to form an output signal in accordance with the desired region of primary medical interest for controlling the dose rate, and/or for automatically ceasing an x-ray exposure. As a consequence of this structure, such a matrix can only be interrogated in a fixed mode, namely serially, which results in limitations in the interrogation speed.

An x-ray diagnostics installation is disclosed in European Application No. 0 217 456 of the type described above, wherein a plurality of measuring fields having variable shape can be selected, so that the selected measuring field is optimally adapted to the prevailing conditions. This enables a high interrogation speed.

SUMMARY OF THE INVENTION

It is an object of the present invention to provide an x-ray diagnostics installation wherein a precise back-projection of the selected region of primary medical interest into the optical beam path between the output screen of the x-ray image intensifier and the input of the video camera can be achieved, so that an exact reproduction of this region of primary medical interest is achieved in the television picture.

The above object is achieved in accordance with the principles of the present invention by arranging a passive light waveguide bundle within the main fiber optics system, the light waveguides in the passive bundle being connected to individually switchable light sources (transducers) at their output side, for gating the desired region of primary medical interest into the television picture.

In the x-ray diagnostics installation disclosed herein, it is possible to allocate individual opto-electric transducers to the fibers of the fiber optics at the output side, so that a predetermined transducer configuration is formed, wherein the transducers are interrogated in parallel, and their signals can be combined to form a total signal.

The transducers, together with the following circuit, can be removably connected to the fiber optics system, so that the output image of the x-ray image intensifier at the output of the fiber optics can be directly observed via a viewing optics.

DESCRIPTION OF THE PREFERRED EMBODIMENTS

Figure 1:
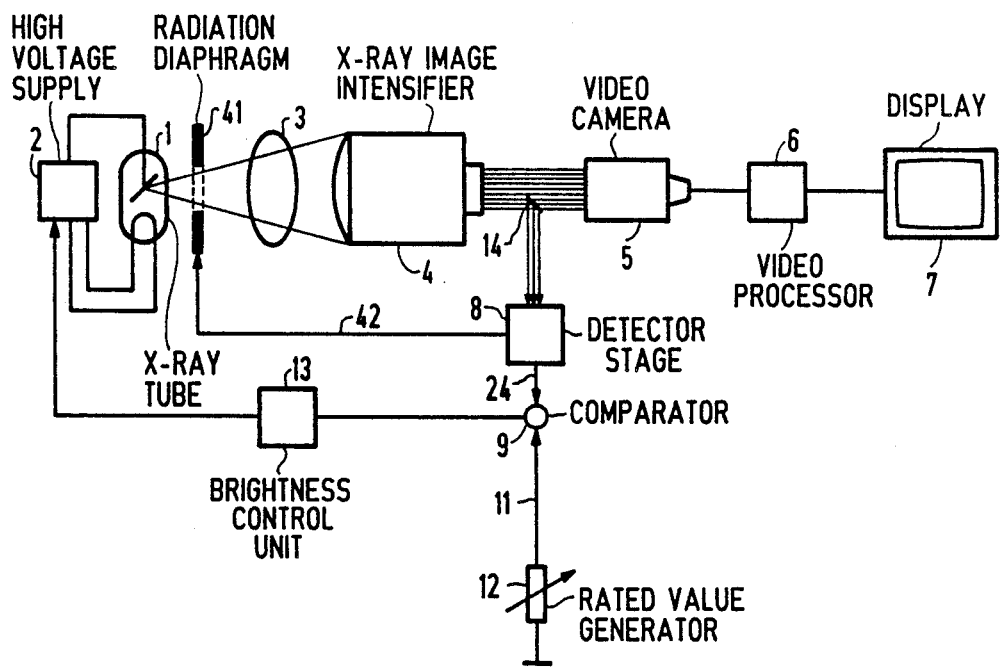
FIG. 1 is a schematic block diagram of x-ray diagnostics installation constructed in accordance with the principles of the present invention.
Figure 2:
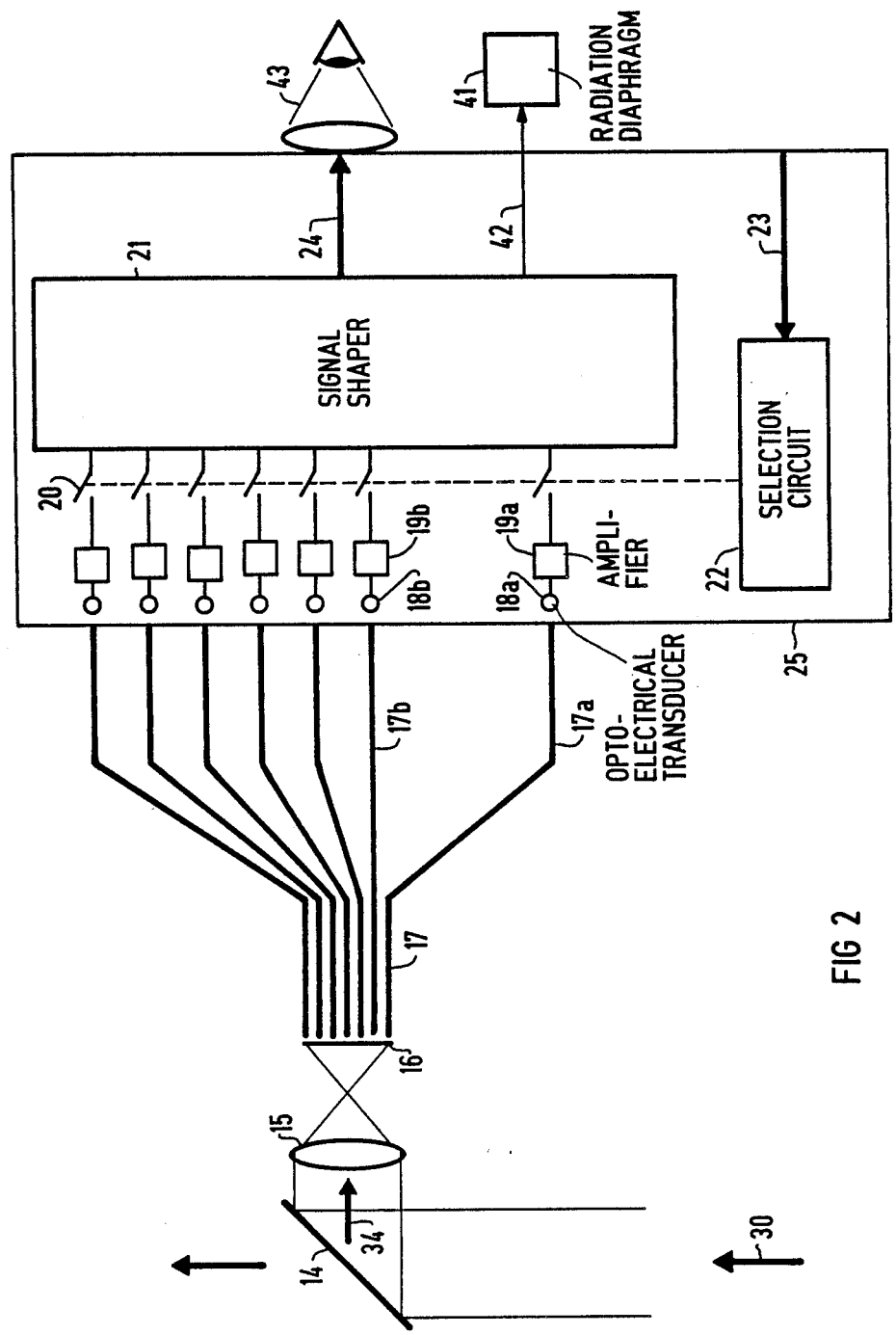
FIG. 2 is a detailed block diagram of the detector 8 shown in FIG. 1.

An x-ray diagnostics installation constructed in accordance with the principles of the present invention is shown in FIG. 1, which includes an x-ray tube 1 which is fed by a high voltage supply 2. A patient 3 is transirradiated by the x-rays generated by the x-ray tube 1. Radiation attenuated by the patient 3 is incident on the input screen of an x-ray image intensifier 4. The intensified image appearing at the output screen of the x-ray image intensifier 4 is picked-up by a video camera 5 and is reproduced on a display 7 via a video processor stage 6. In order to maintain the average image brightness within a measuring field of the output screen of the x-ray image intensifier 4 at a constant level, a detector stage 8, shown in greater detail in FIG. 2, is provided as an actual value generator, which supplies a signal corresponding to the actual brightness value to an input of a comparator 9. The comparator 9 is supplied at an input 11 with a rated value corresponding to a desired average image brightness within the measuring field of the output screen of the x-ray image intensifier 4. A signal corresponding to the difference, if any, between the rated value and the actual value is supplied as an output signal from the comparator 9 to an input of a brightness control unit 13 of known construction. Dependent on the magnitude of the signal from the comparator 9, the brightness control stage 13 modifies the output of the high voltage supply 2 so that the actual value is matched to the rated value. The rated value supplied to the comparator 9 is set by a rated value generator 12.

The detector stage 8 is supplied with a portion of the light from the output screen of the x-ray image intensifier 4 by a semi-reflecting mirror 14 disposed in the light beam path between the output screen of the x-ray image intensifier 4 and the video camera 5. The detector stage 8 includes suitable input optics 15 so that the output image from the x-ray image intensifier 4 is projected in a plane 16 which contains the ends of a fiber optics system 17, consisting of a plurality of individual light waveguides 17a, 17b, etc. The opposite ends of the light waveguides 17a, etc. have optoelectrical transducers 18a, 18b, etc. allocated thereto, which supply electrical output signals corresponding to the received brightness. The input signal of the comparator 9 is formed from these output signals via preamplifiers 19a, 19b, etc., a switching bank 20 and a signal shape 21. The switches of the switching bank 20 are driven by a selection circuit 22, having an input 23 supplied with a signal corresponding to the desired region of primary medical interest within the output image of the x-ray image intensifier 4. The fiber optics system 17 is fanned out at its output side allocated to the transducers 18a, etc., so that an individual allocation of a transducer 18a, etc. to a respective light waveguide 17a, etc. is possible. For forming the region of primary medical interest, the switches of the switching bank 20 which correspond to this desired region are closed. The signal shape 21, at its output 24, forms the signal supplied to the comparator 9, and corresponding to the mean dose rate within the region of primary medical interest. This signal is formed by combining the input signals to the signal shape 21.

The arrangement shown in FIG. 2 can also serve as an adjustment circuit for setting the position of the region of primary medical interest with reference to the patient plane. For this purpose, a phantom provided with suitable markings is arranged in front of the x-ray image intensifier and is irradiated with x-rays, so as to be imaged on the output screen of the x-ray image intensifier 4, and thus also in the plane 16. The adjustment takes place by displacing the entrance face of the fiber optics system 17 in the plane 16. For this purpose, the components contained within the block 25 are constructed as a removable unit, so that the phantom image can be directly seen at the outputs of the light waveguides 17a, etc., when a sufficient number of light waveguides 17a, etc. are used. Passive light waveguides without transducers can also be used, in addition to the active light waveguides with transducers. It is also possible to employ a light waveguide fiber skein which contains active and passive fibers in the plane 16, and splits those groups of fibers into a active skein having permanently attached transducers, and into a passive skein without transducers. The active skein is then fanned out, whereas the passive skein can be used with the same diameter as the plane 16. The passive skein will then contain recesses at those locations which are occupied by the active fibers in the plane 16, and is guided to a suitable location in the housing of the mirror 14. The position of the measuring fields can thus be recognized and adjusted, because the phantom markings can be brought into coincidence with the gaps in the image which the passive skein supplies. A viewing optics 43 for matching and magnification may be used so that the foregoing can be done under visual control.

In the exemplary embodiment of FIG. 1, the output signal from the detector stage 8 serves to control the dose rate, as described above. In an automatic exposure unit, it can also be used as the actual value signal for automatically switching x-ray exposures. The light from the light waveguides at the outer edge of the image can be monitored so that an output signal based on this light is generated at line 42, with a radiation diaphragm 41 being driven with this output signal to avoid lateral blooming.

Figure 3:
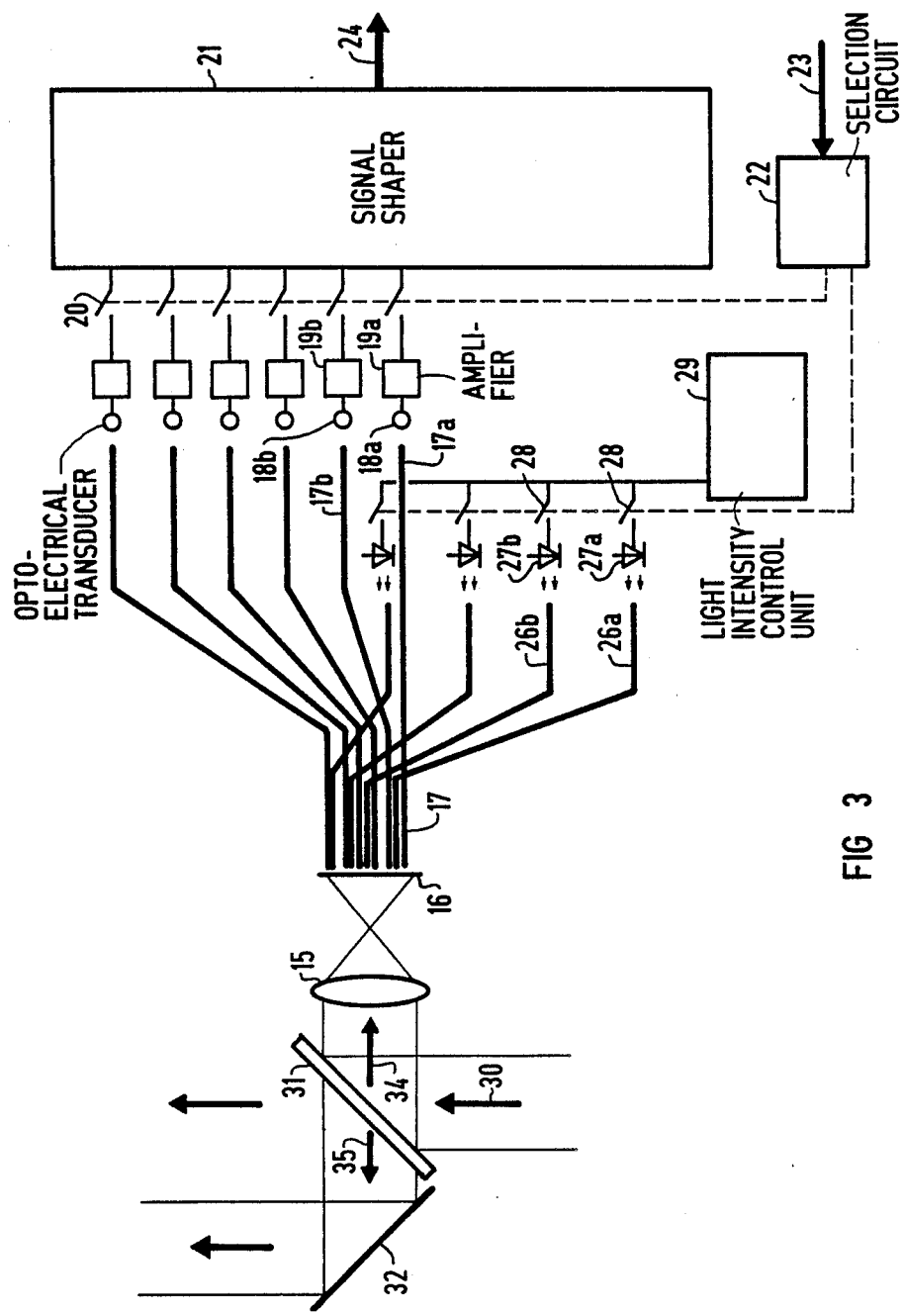
FIG. 3 is a schematic block diagram of a further embodiment of the detector 8.

A modification of the embodiment shown in FIG. 2 is shown in FIG. 3 wherein passive light waveguides 26a, 26b, etc. are provided in addition to the other components which are provided with the same reference symbols as used in FIG. 2 The passive light waveguides 26a, 26b, etc. are used for back-projection of the region of primary medical interest into the light beam path between the output screen of the x-ray image intensifier 4 and the video camera 5. Dependent on the selected region of primary medical interest, i.e., dependent on the activated transducers 18a, etc., selected by the switching stage 20, the light waveguides 26a, etc., combined with the active light waveguide 17a, etc. in the fiber optics 17, are illuminated by a corresponding selection of light emitting diodes 27a, 27b, etc. To this end, the light emitting diodes 27a, etc. are driven by a selection circuit 22 via a switching bank 28. A light intensity control unit 29 allows adjustment of the light intensity of the light emitting diodes 27a, etc.

As in FIG. 2, the light from the x-ray image intensifier 4 arrives in the direction of arrow 30, and a partially reflecting mirror 31 directs a portion of the light in the direction of the arrow 34 to the plane 16. The mirror 31 allows a small percentage of the incident light to pass in the direction toward the video camera 5. The output light from the light waveguides 26a, etc. proceeds through the input optics 15 and through the partially reflecting mirror 31 in the direction of the arrow 35 onto a mirror 32, which directs the light in a direction toward the video camera 5. Accordingly, a superimposition of the output image of the x-ray image intensifier 4 and of the image of the picture elements lighted in the plane 16, and formed by the ends of the light waveguides 26a, etc., is obtained in the displayed television picture. This image represents the region of primary medical interest selected using the selection circuit 22.

Figure 4:
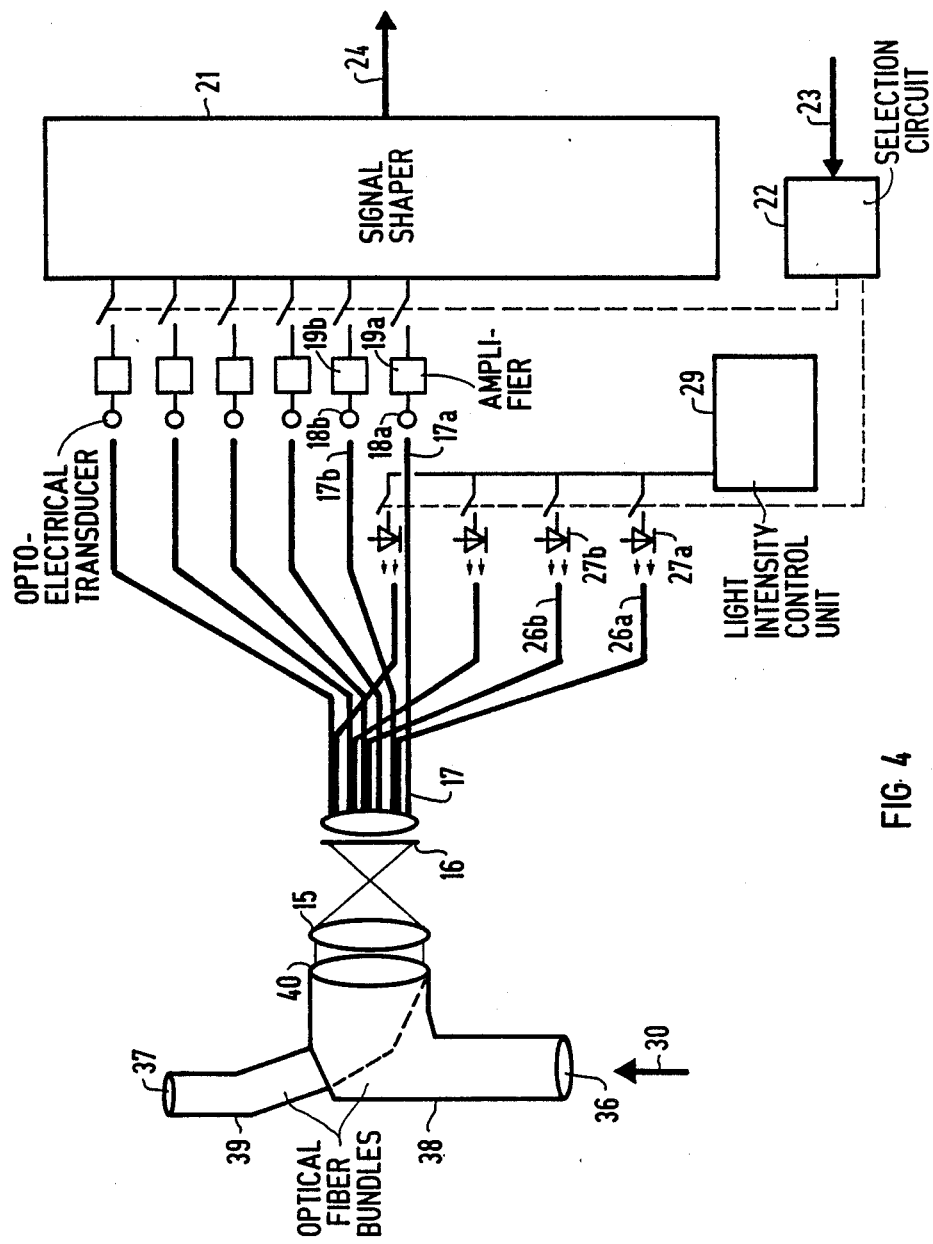
FIG. 4 is a schematic block diagram of another embodiment of the detector 8.

In a further embodiment shown in FIG. 4, an optical fiber bundle is provided which proceeds from a common end 40 of the input optics 15 and branches into two sub-bundles 38 and 39 in the beam path between the output screen of the x-ray image intensifier 4 and the television camera 5. This optical fiber bundle is used instead of the mirrors 31 and 32 in the embodiment of FIG. 3. At its input side, the subbundle 38 receives a portion of the output light from the output screen of the x-ray image intensifier 4, and forwards this light via the input optics 15 to the active light waveguides 17a, etc. The light waveguides 26a, etc. project the light via the input optics 15 and the common end 40 into the subbundle 39, which conducts the light via aperture 37 into the beam path in the direction toward the video camera 5. Thus it is possible to mix the selected region of primary medical interest into the television picture.

A combination of conventional multiplier optics having a mechanically switchable region of primary medical interest with a corresponding display, separated therefrom, is also possible via the fiber optic bundle 39. The image of the region of primary medical interest in the plane 16 can be generated by another arrangement, for example, by a transparent LCD matrix, instead of being generating by the combination of the components 27a, etc. and 26a, etc., while retaining the light intensity control 29 and the switching bank 28.

Although modifications and changes may be suggested by those skilled in the art, it is the intention of the inventors to embody within the patent warranted hereon all changes and modifications as reasonably and properly come within the scope of their contribution to the art.

We claim as our invention:
1. An x-ray diagnostics installation comprising:
   means adapted for exposing an examination subject to a dose of x-radiation;
   an x-ray image intensifier having an input screen on which x-radiation attenuated by said examination subject is incident and an output screen which generates a light image in a light beam path corresponding to the incident x-radiation;
   video pick-up means disposed in said light beam path for converting said light images into electrical signals;
   video processing and display means connected to said video pick-up means for generating a video image from said electrical signals corresponding to said light image;

first fiber optics consisting of a plurality of light waveguides having an input end disposed for receiving light in said light beam path, and having an output end;

a plurality of opto-electrical transducers disposed at said output end of said first fiber optics and respectively associated with said light waveguides;

switching means for selectively activating said plurality of opto-electrical transducers in a pattern corresponding to a region of primary medical interest within said light image for obtaining a signal corresponding to the average brightness in said region of primary medical interest;

means for controlling the dose of x-radiation from said means for exposing based on said average image brightness;

a plurality of electro-optical transducers also selectively activated by said switching means in said pattern, so that said electro-optical transducers in combination form a light image of said region of primary medical interest; and second fiber optics in optical communication with said electro-optical transducers for back-projecting said light image of said region of primary medical interest into said light beam path for inclusion in said video image.

2. An x-ray diagnostics installation as claimed in claim 1, further comprising optical viewing means disposed for obtaining a direct optical image at said output end of said first fiber optics.

* * * * *